United States Patent [19]

Kling et al.

[11] 4,166,095

[45] Aug. 28, 1979

[54] SELECTIVE TEST SELECTION AND INDICATOR MEANS IN AN AUTOMATIC CHEMICAL TESTING APPARATUS

[75] Inventors: Gary W. Kling; Scott C. Swanson, both of Houston, Tex.

[73] Assignee: Hycel, Inc., Houston, Tex.

[21] Appl. No.: 936,416

[22] Filed: Aug. 24, 1978

[51] Int. Cl.² .................. G01N 33/16; G01N 1/18
[52] U.S. Cl. ............................... 422/67; 364/497
[58] Field of Search .............. 23/253 R, 259, 230 R; 364/497, 498

[56] References Cited

U.S. PATENT DOCUMENTS

| | | | |
|---|---|---|---|
| 3,728,079 | 4/1973 | Moran | 23/253 R |
| 4,043,756 | 8/1977 | Sommervold | 23/253 R X |
| 4,052,161 | 10/1977 | Atwood et al. | 23/253 R X |
| 4,095,272 | 6/1978 | Janzen | 23/253 R X |

Primary Examiner—R. E. Serwin
Attorney, Agent, or Firm—Robert P. Cogan

[57] ABSTRACT

In an automatic chemical testing apparatus in which different chemical tests are performed selectively on one or more aliquots of each of a number of samples, samples are placed in successive ordinal positions for sequential aspiration into the apparatus for testing. Selection means in a selection panel are actuated to enable a position, i.e. to enable storage of instructions for tests to be performed on a sample in a particular ordinal position after it is aspirated into the apparatus. Test selection means are operated to program tests to be performed for the sample in the enabled position. Indicator means, e.g. lamps, are energized to indicate which position is enabled and which positions have been programmed. A further display indicates which tests have been programmed for an enabled channel.

9 Claims, 14 Drawing Figures

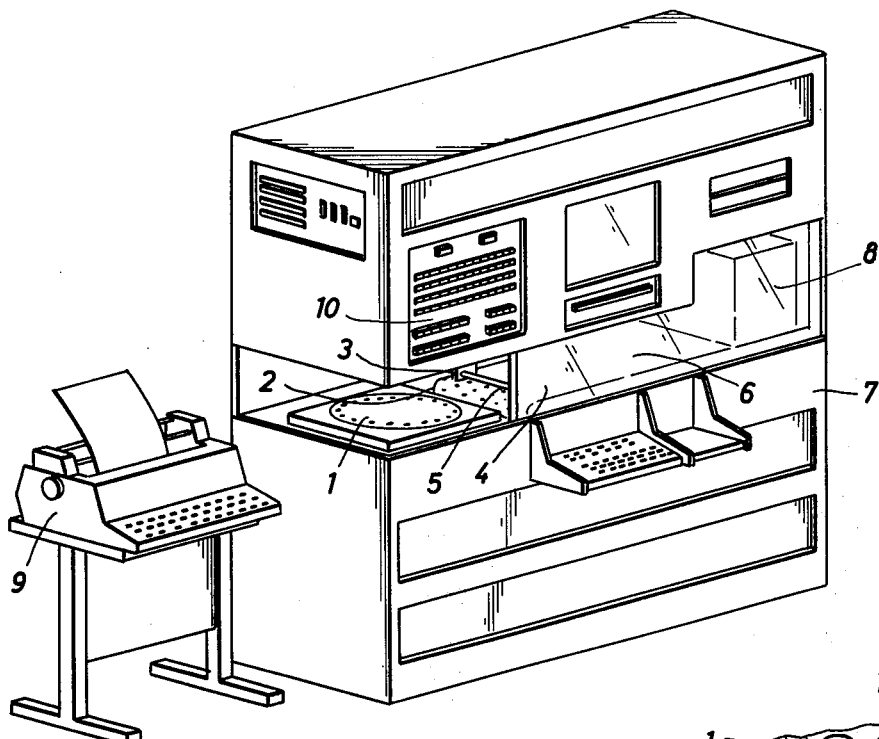
FIG. 1
FIG. 2
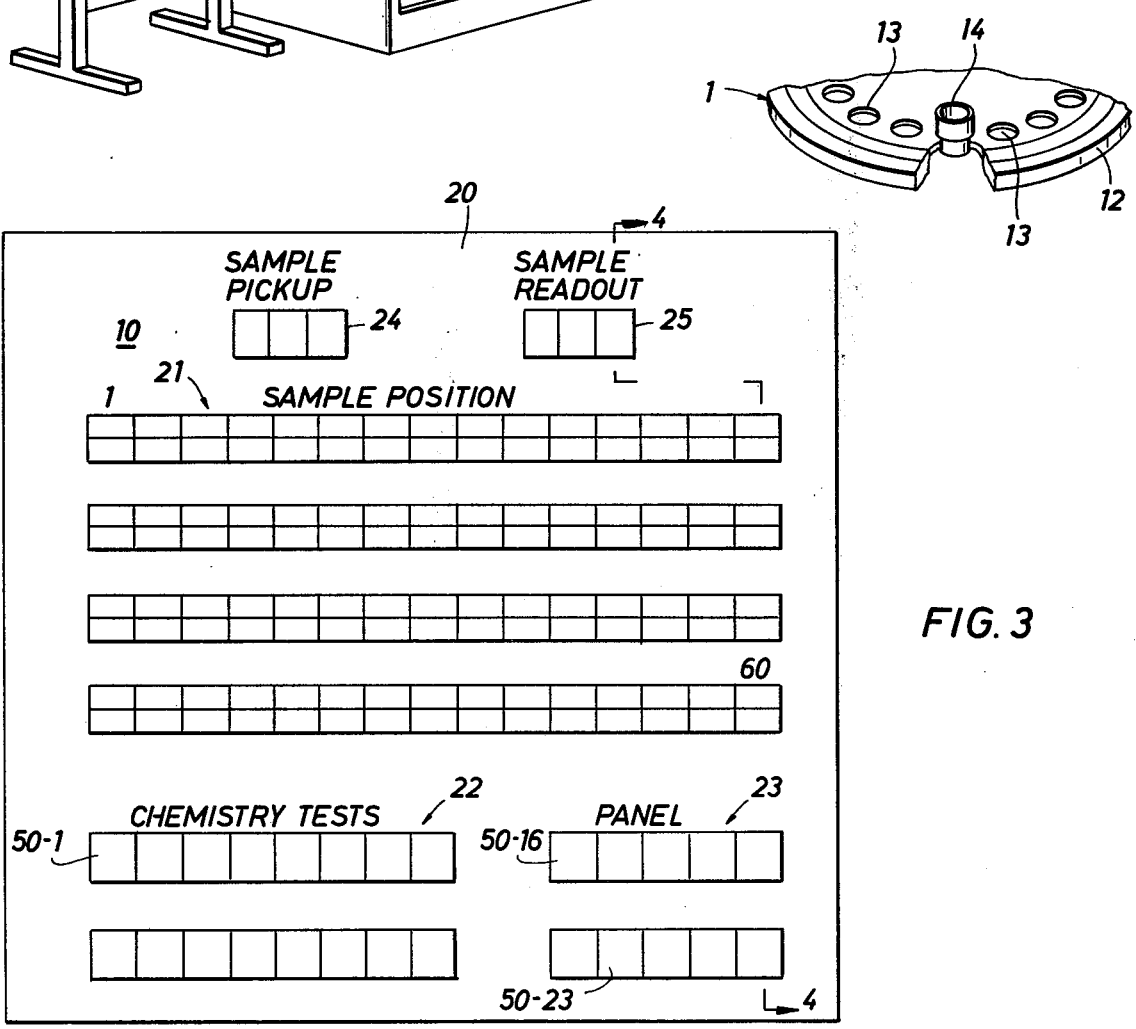
FIG. 3

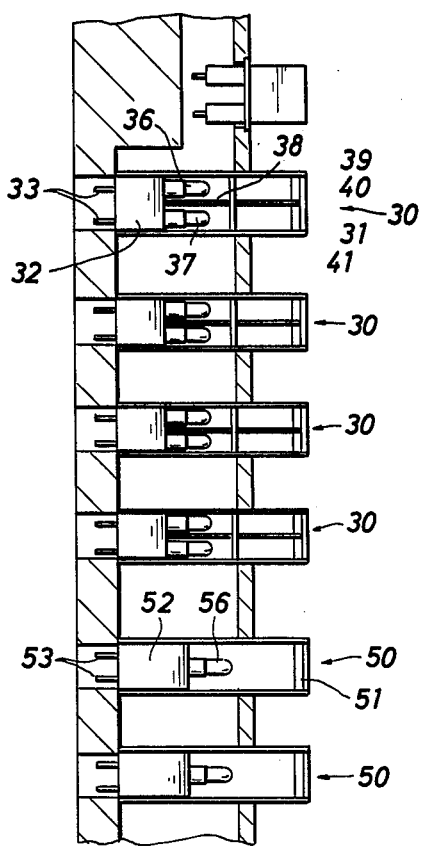
FIG. 4
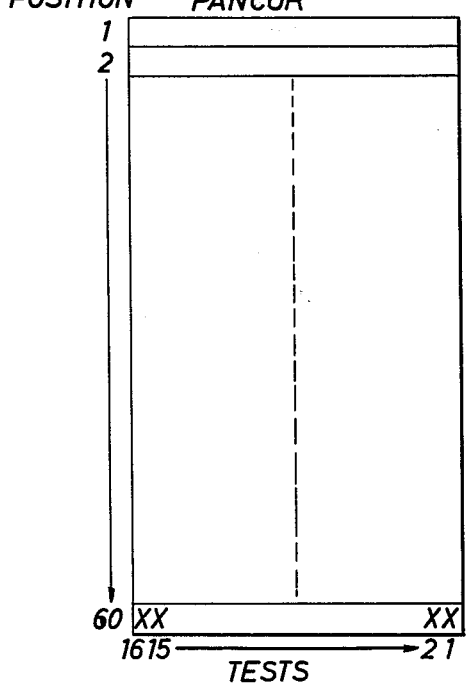
FIG. 12
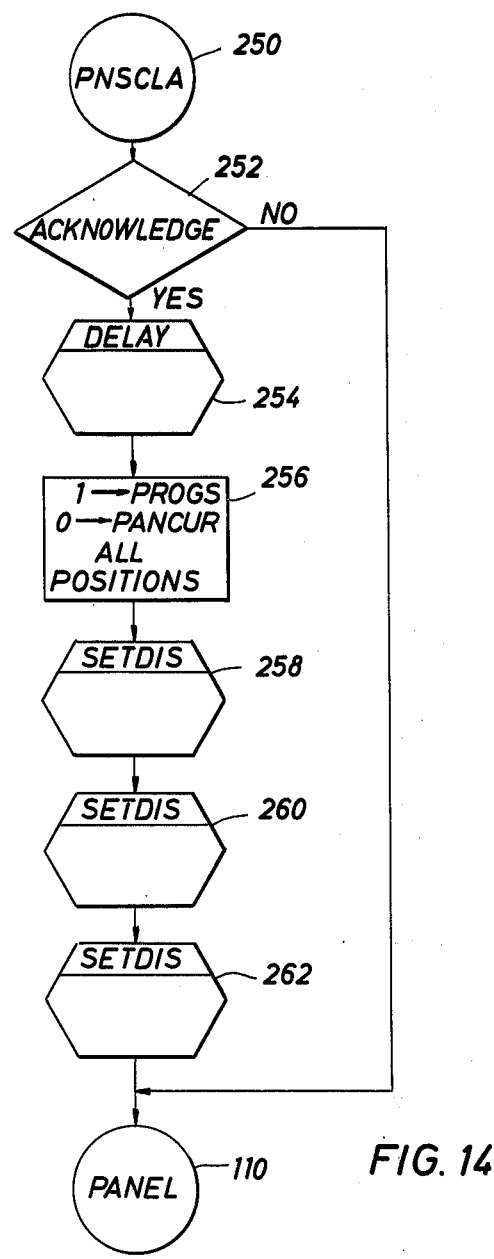
FIG. 14
FIG. 13

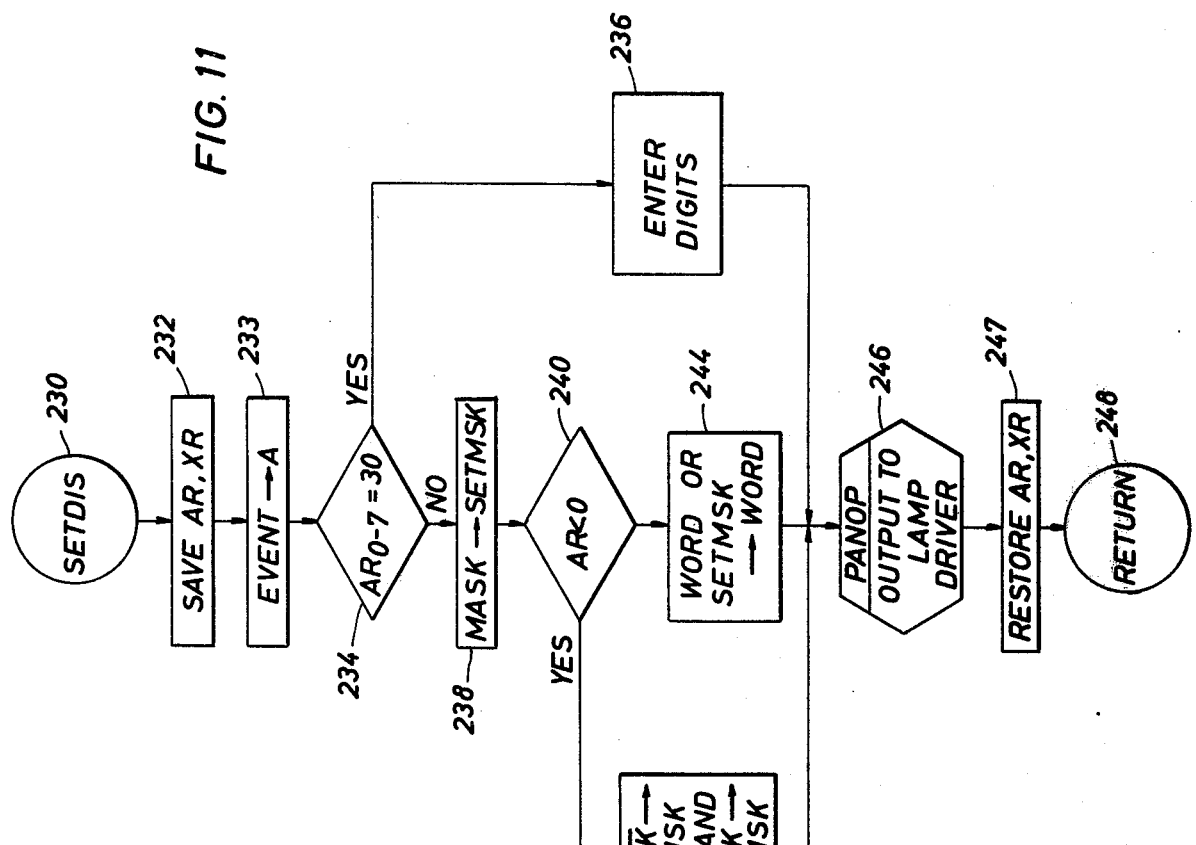
FIG. 11
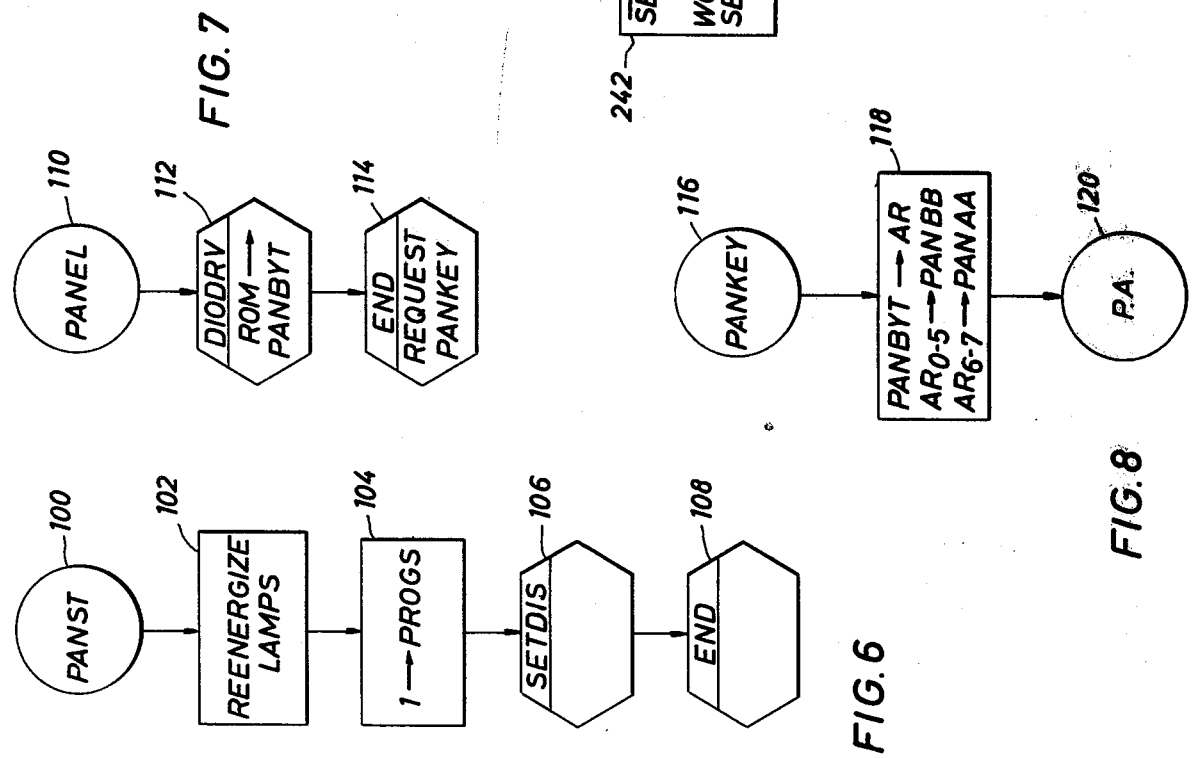
FIG. 7
FIG. 8
FIG. 6

SELECTIVE TEST SELECTION AND INDICATOR MEANS IN AN AUTOMATIC CHEMICAL TESTING APPARATUS

BACKGROUND OF THE INVENTION

This invention relates to automatic chemical testing apparatus, and more particularly to test selection and indicator means therein.

The context for the present invention is the type of chemical analyzer in which a number of samples are provided, each to have a selected number of different chemical tests performed thereon. The number of tests performed on one chemical sample may differ from the number of tests performed on another chemical sample. Preferably the samples are placed in means for holding a plurality of samples. A different test is performed on each of a number of aliquots of one sample. Test selection means are operated to produce instructions to the apparatus. Selected aliquots are each reacted with particular reagents injected therein in response to the instructions. At a subsequent time, reacted aliquot and reagent mixtures are measured for a change to indicate the results of each of the tests, as, for example, by spectrophotometric analysis. An example of a highly effective apparatus is disclosed in commonly assigned U.S. Pat. No. 3,728,080 to John J. Moran issued on Apr. 17, 1973, the disclosure of which is incorporated herein by reference. A further form of such apparatus is disclosed in commonly assigned U.S. Pat. No. 4,043,756 to David E. Sommervold issued Aug. 23, 1977, the disclosure of which is also incorporated herein by reference. The apparatus disclosed in both these patents successfully performs all of above-recited functions. In accordance with the present invention, it is desired to provide further convenience and efficiency in an operator's operation and use of the test selection means, including displaying to the operator which tests have been selected for each sample in a manner to further facilitate use of the test selection means.

SUMMARY OF THE INVENTION

It is therefore an object of the present invention to provide, in an automatic chemical testing apparatus including means for commanding and performing a selected number of tests on each of a plurality of chemical samples, test selection means which are simplified in construction and test selection indicator means which may be conveniently utilized by an operator.

Briefly stated, in accordance with the present invention, in an automatic chemical testing apparatus including means for programming and performing a selected number of different tests on aliquots of each of a number of chemical samples and in which each sample is associated with a position corresponding to the order in which the sample is tested, there are provided position selection means for enabling selection of tests for the sample associated with that position, test selection means for programming tests to be performed on a selected sample after a position is selected, an indicator means responsive to actuation of each of the selection means for indicating which position is currently enabled, indicator means associated with each position for indicating which positions have had tests programmed therefor, and test indicating means associated with the test selection means for indicating which tests have been selected for a current enabled position.

BRIEF DESCRIPTION OF THE DRAWINGS

The means by which the foregoing objects and features of invention are achieved are pointed out with particularity in the claims forming the concluding portion of the specification. The invention, both as to its organization and manner of operation, may be further understood by reference to the following description taken in connection with the following drawings.

Of the drawings:

FIG. 1 is an illustration of an automatic chemical testing apparatus incorporating the present invention;

FIG. 2 is an illustration, partially broken away, of a sample table for providing chemical samples in time sequence for testing;

FIG. 3 is an illustration of a control panel including test selection and indicator means in accordance with the present invention;

FIG. 4 is a partial cross-sectional view taken along lines IV—IV of FIG. 3;

FIGS. 6–11 are flowcharts useful in understanding the operation of the present invention and defining the structure of the computer included therein; and FIGS. 12 and 13 are charts illustrating storage of test instructions within the present invention.

FIG. 14 is an illustration of a master clear routine.

DESCRIPTION OF THE PREFERRED EMBODIMENTS

Figure 5:
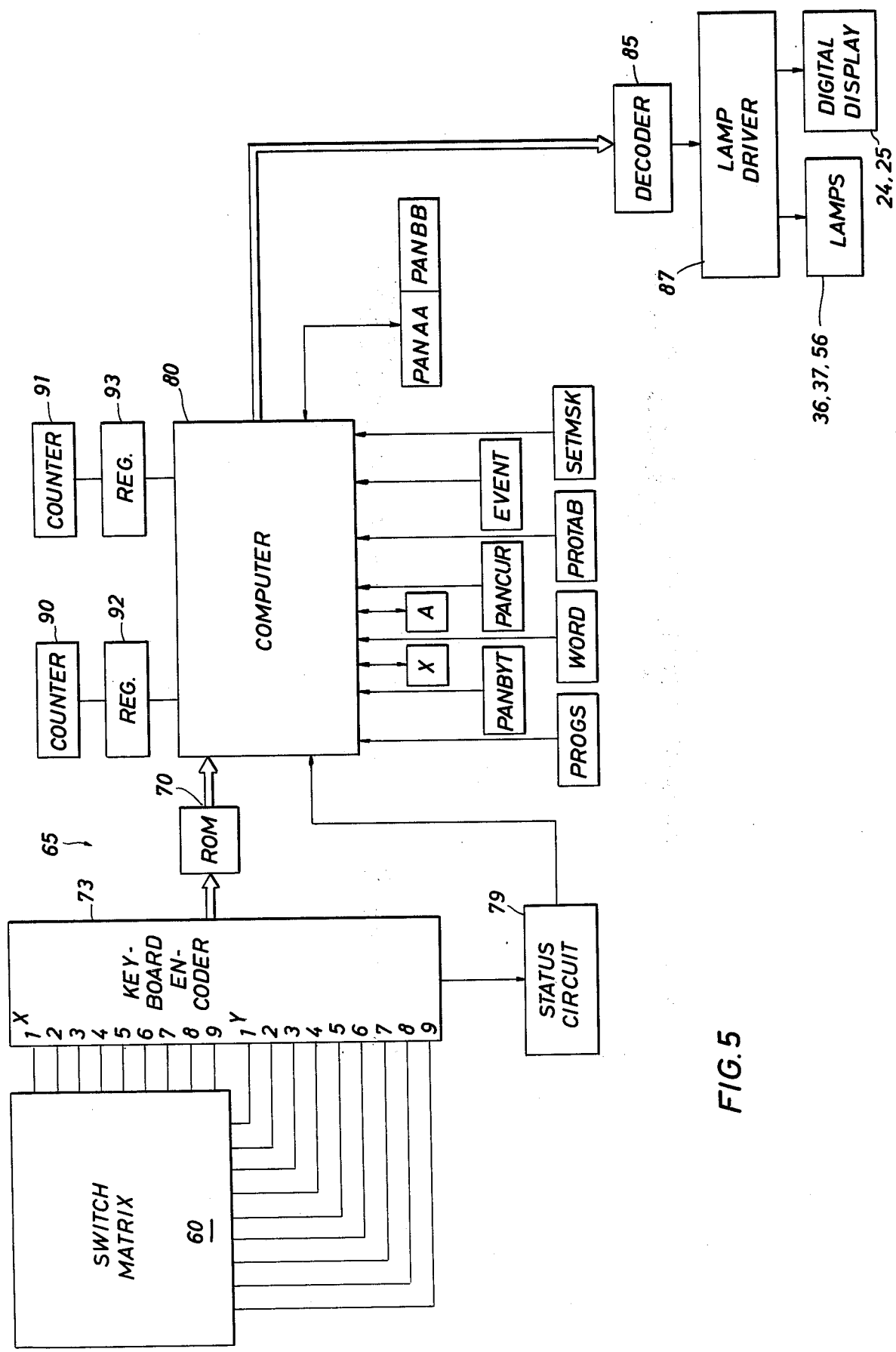
FIG. 5 is a circuit diagram, partially in schematic and partially in block diagramatic form, of the present invention.

Referring to FIG. 1, there is illustrated an automatic chemical testing apparatus incorporating the present invention. The automatic chemical testing apparatus may be constructed in accordance with the above-cited patents to Moran and Sommervold. A sample station 1 is provided at which a number of chemical samples may each be placed for sequential processing. Aliquots from one sample at a time are delivered to a reaction conveyor 2 by fluid transfer means 3. The reaction conveyor 2 includes in the preferred embodiment a plurality of parallel slats 4, each extending in a transverse direction and which are periodically indexed a predetermined distance in a longitudinal direction. Each slat 4 supports a plurality of reaction containers 5, each of which may receive an aliquot of a sample. The slats 4 are indexed through a reaction station 6 comprising incubation means and reagent injecting means, and at a selected time or times, selected reagent or reagents are dispensed into selected sample containers 5 from a reagent source station 7. At an analysis station 8 including readout means, reacted contents are aspirated from each sample container 5, and chemical testing is performed thereon to determine the concentration of each substance for which a test is being performed. Spectrophotometric measurement is the most common form of measurement made on the reacted contents from each reaction container. However, other forms of measurement such as nephelometry could be utilized. Hard copies of test results are provided on a printer 9. However, any well-known utilization means may be utilized for providing the test result output. Hard copy printouts are not always necessarily utilized. Test results could be directly electronically interfaced to a laboratory computer (not shown). In order to achieve the selective testing performed by the present invention, test selection means in a control station 10 constructed in accordance with the present invention are provided. In accordance with the present invention, simplified construction in the test selection means and means for indicating to the operator which tests have been selected for which samples are provided.

Identification of each sample to be tested is described with respect to FIG. 2, which is an axonometric view, partially broken away, of a sample table 12 included in the sample station 1. In the present embodiment, the sample table 12 is a circular table having sixty equiangularly spaced apertures 13, each for receiving a sample container 14. The sample table 12 is periodically rotated one position in synchronism with indexing of the slats 4 of the reaction conveyor 2 for periodically presenting a new sample to the fluid transfer means 3. As indicated in FIG. 2, each of the apertures 13 may be consecutively numbered 01 through 60. Each sample may be identified by the position in which the sample container 14 containing that sample is placed. For processing of more than sixty samples, each sample may be identified by the ordinal position in the sample table 12 and the revolution of the sample table 12. It is, of course, contemplated that sample containers 14 will be removed from sample table 12 after the sample has been delivered to the fluid transfer means 3. Thus, for example, during a first revolution of the sample table 12, the sample in the sample container 14 placed in the aperture 13 having the number 05 may be referred to as the sample in position 105. Test instructions are stored for a sample in a particular ordinal position. The tests are performed after that particular sample has been drawn into the fluid transfer means 3 and aliquots thereof delivered to the reaction conveyor 2. Therefore, for purposes of a description of the preferred embodiment, the selecting of tests for a particular sample will be referred to as programming a position. However, the invention is directed to test selection and display of selected tests. The particular form of sample station 1 utilized may take many other forms. It is also possible to use means other than a sample station 1 for delivery of samples to the reaction conveyor 2.

Operation by an operator of the control station 10 is described with respect to FIGS. 3 and 4; the circuitry of the present invention is described with respect to FIG. 5. Operation of the circuitry is described with respect to FIGS. 6—13.

FIG. 3 is a partial elevation of FIG. 1 illustrating the control station 10. The control station 10 includes a panel 20. To select tests, an operator makes a selection within a position selector group 21 to enable one position, and then selects tests from within a test selector group 22. A function selector group 23 is provided for selection of groups of tests or other functions such as reset described below. Additionally, displays 24 and 25 may be provided for indicating respectively the sample table position identification of the samples currently at the fluid transfer means 3 and at the analysis station 8. The displays 24 and 25 preferably comprise three digit decimal displays.

Further description of the control station 10 is made with respect to FIGS. 3 and 4 taken together. FIG. 4 is a partial cross-sectional view taken along lines IV—IV of FIG. 3. The position selector group 21 preferably comprises a plurality of switching means as well as first and second indicator means each associated with one sample position. In the present embodiment, sixty switching and indicator means 30 are provided, and may be individually identified as 30-1 through 30-60, for selection of a position 01 through 60 respectively. As seen in FIG. 3, the switching and indicator means 30 are arrayed in four rows of fifteen each. Each switching and indicator means 30 comprises an actuating button 31 mechanically coupled for actuating a switch 32 having terminals 33 connected as described with respect to FIG. 5 below. First and second indicators means, lamps 36 and 37, preferably are mounted to the switch 32 in a chamber defined by the button 31. A separating wall 38 in the button 31 defines first and second chambers, each housing one lamp 36 or 37. First and second color filters 39 and 40 may be placed behind a transparent or translucent front face 41 of the switch button 31. Many constructions are well-known in the art such that the wall 38 is provided while still allowing for reciprocal movement of the switch button 31. Alternatively, the lamps 36 and 37 may be positioned on the panel 10 and not in a switch button 31. In the preferred embodiment, the switch button 31 is spring loaded so that it may be depressed and will return to the position as shown in FIG. 4. The lamp 36 is illuminated when the particular sample to which the switch and indicating means 30 it is included in corresponds is selected for enabling of test selection. The lamp 37 is deenergized when another position is selected for programming. The lamp 37 is energized when tests have been programmed for the position in which the switch and indicator means 30 corresponding to that position has been programmed and remains illuminated until cleared or until the tests are performed and completed.

The tests selector group 22 and function selector group 23 each include selection and indicator means 50 preferably comprising a hollow pushbutton 51 mechanically connected for operating a switch 52 having terminals 53. A lamp 56 means is included for connection to selected ones of terminals 53. The button 51 is preferably spring-loaded so that it may be depressed and will return to the position as shown in FIG. 4. In the present embodiment, sixteen different tests may be provided, and sixteen selection and indicator means 50 are provided in two rows of eight each. Once a position is enabled, each of the selection and indicator means 50, which may be referred to as 50-1 through 50-16 and whose corresponding components may be denoted with suffixes -1 through -16, may be depressed to select and program a test as further described with respect to FIG. 5. The lamp 56 therein is illuminated to indicate that test has been programmed for that position. The lamp will be illuminated each time that test has been programmed for the position which is currently enabled. In the function selector means 23, five switch and selection means 50 are included, 50-17 through 50-21 which may be each used to command a group of tests in the manner described with respect to FIG. 5 below. The function selector group 23 also includes further function selection means 50, 50-22 through 50-26. The switch 50-22 may be used for commanding all tests, i.e., a profile, at once, the switch 50-23, called an "enter" selector may be used for energizing a successive one of the selection and indicator means 30 in the sample selector group 21 and deenergizing a currently energized indicator; switch 50-23 may be utilized for reset; switch 50-24 may be utilized for a master clear function; and switch 50-26 may be utilized to test all lamps. In the present embodiment, the switches 32 and 52 are of the type that toggle on each operation. A first or subsequent odd operation is an actuation of the switch 32 or 52. Alternate operations deactivate each switch.

In operation, to select and program tests, an operator selects one of the position selection and indicating means 30 and actuates it. This results in the lamp 36 therein being illuminated to indicate a currently enabled position. The operator may depress selected buttons 51 of selection and indicating means 50 within the test selector group 22 to select and program tests for that position and to illuminate the corresponding lamp 37. The lamp 56 within each button 51 in the test selection means 22 is illuminated to indicate which test has been programmed for a currently enabled position. Alternatively, one of the buttons 51-16 through 51-21 may be selected to select groups of tests, occasionally also referred to as panels. For example, certain tests may be associated with a cardiac panel, renal panel or other panel. When one of the buttons 51-17 through 51-21 is depressed, the lamps 56-1 through 56-16 corresponding to the individual test comprising that panel are also illuminated. The lamp 56 in the panel button is also illuminated. Alternatively, the operator may depress button 51-22 which is utilized for commanding profiles. In other words, all tests are programmed, and all the lamps 56-1 through 56-16 are illuminated.

In order to program another position, the operator may depress any other button 31-1 through 31-60 or depress the enter button 51-23. Depression of the enter button 51-21 will enable the next consecutive position. The first lamp 36 is deenergized, and the lamp 36 for the current enabled position is energized. The lamp 37 for the previously programmed position remains illuminated to indicate a position for which tests have already been programmed. Operation proceeds in the above-described manner. The reset button may be used to remove test selection entries made for a current enabled position. To review tests selected for any particular channel, the switch button 31 associated therewith is depressed, and the circuitry of FIG. 5 operates to energize the particular ones of lamps 56-1 through 56-16 corresponding to tests which have been selected.

FIG. 5 is a circuit diagram, partially in schematic and partially in block diagramatic form of the present invention. The same reference numerals are used in FIG. 5 to correspond to components denoted by the same reference numerals in FIGS. 3 and 4. A switch matrix 60 is provided comprising all of the switches 32 and 52 connected in a 9×10 switching matrix. Closing any one of the switches in the switching matrix 60 closes the circuit between any one of nine terminals, called X1 to X9, and any one of ten terminals called Y1 to Y10. In this manner, each switch 32 or 52 when closed produces a unique signal as represented by the particular X and Y terminals which it connects.

The switching matrix 60 is connected to instruction means including a decoder means 65 which translates each switching matrix output to an eight bit digital signal uniquely indicating the particular switch 32 or 52 which was actuated. This eight bit digital representation is provided at a parallel output 70. The decoder means 65 also provides a status output signal at a terminal 71 which signal is indicative of one particular switch 32 or 52 having been actuated. The decoder means 65 may take many well-known forms. In the present embodiment, the decoder means 65 comprises a keyboard encoder 73 having an input connected to the switching matrix 60 and an output connected to a read-only memory 74 which in turn has an output connected to the parallel output 70. The keyboard encoder 73 provides a unique address indicating which switch 32 or 52 was activated. The address is connected to the read-only memory 74 which produces the eight bit number to be provided at the parallel output 70. Outputs could be provided directly from the keyboard encoder 73. However, use of the read-only memory 74 facilitates production of an eight bit output in the following manner.

The eight bit output may be viewed as being in the form AABBBBBB, where the digit on the left is the most significant digit and the digit on the right is the least significant digit. Preferably, the read-only memory 74 is loaded such that the digits in positions AA produced will be 00 when a sample number is selected, the digits AA will be 01 when one of the buttons in the test selection means 22 is depressed, and the digits AA will be 10 when one of the switches 52 in the function selection means 23 is activated. For further convenience, the read-only memory 74 is loaded such that when AA equals 0, then BBBBBB in binary form corresponds to the decimal value of the particular switch 32-1 through 32-60 which is activated. When AA equals 01 then BBBBBB equals the number of the particular switch 52 in the test selection means 22 which is activated, and when AA equals 10 then BBBBBB equals 0 for a profile, one value of 1 through 5 for one of the group selection buttons 50-17 through 50-21, 6 for enter, 7 for reset and 8 for master clear.

The terminal 71 of the decoder means 65 is connected to a status circuit 79. Both the status circuit 79 and the decoder means 65 are connected to a programmed digital computer 80 which may, for example, comprise an LSI-2 computer manufactured by Computer Automation, Inc., Irvine, California. The parallel output 70 is connected to a data input of the computer 80. The status circuit 79 is a well-known gate circuit interconnected to the computer 80 to request service and response to actuation of a switch 32 or 52 and for receiving and acknowledging output from the computer 80. The computer 80 includes various registers which are labeled PROGS, PANCUR, A, X, CTR and GRP for storing particular values during operation as described below. The computer 80 provides outputs from a Word register to a decoder circuit 85 in turn providing an output to a lamp driver circuit 87 which provides outputs for illuminating the displays 24 and 25 (FIG. 1) and illuminating or deenergizing the lamps 36, 37 and 56. The status circuit 79, computer 80 and decoder circuit 85 comprise control means. The Word register in the present embodiment stores eleven sixteen bit words indicative of every display element and the bits therein represent whether a display element is to be illuminated.

Counter means 90 and 91 are provided in the computer 80 for counting machine cycles to indicate the indexing of samples through the reaction conveyor 2, and respectively increment registers 92 and 93, which provide digital representations to the computer 80 indicative of the sample position numbers of the samples respectively at the fluid transfer means 3 and the analysis station 8.

Operation of the circuitry of FIG. 5 is described with respect to FIGS. 6-3. FIGS. 6 through 11 are flow-charts of operation which also define structure and interconnections within the computer 80 as well as defining specific program steps. It is well known in the art that flow diagrams are directly translatable into specific process steps without undue experimentation. For example, see John G. Wester and William D. Simpson, *Software Design For Microprocessors* (Texas Instruments, Inc., Dallas, Texas, 1976). FIGS. 12 and 13 are charts useful in further understanding particular signals described below.

FIG. 6 is a chart of a start-up routine 100 called PANST. According to block 102, all the lamps 36, 37 and 56 are reset to their state during a last period of operation. Next a block 104, the value 1 is loaded in the PROGS register in the computer 80. The value in the PROGS register is indicative of the number of the current enabled position. This will therefore be indicative of enabling the position selector and indicator 30-1 of FIG. 3. At block 106 the SETDIS subroutine, which will be explained in further detail with respect to FIG. 10 below, is followed to illuminate the lamp 36-1 (FIG. 3) to indicate that position 1 is ready for programming. The end of this subroutine indicated at block 108 follows, and the computer 80 then awaits a request for service which will be initiated by an operator by depression of a button 31 or 51 at the control station 10. This request for service starts the panel subroutine 110 illustrated in FIG. 7. At block 112, the byte of information comprising the eight bits at the parallel output 70 of the decoder 65 is delivered to the computer 80 and stored in a PANBYT register, and an instruction is made to request a PANKEY subroutine at the end. The end follows at block 114.

Figure 9:
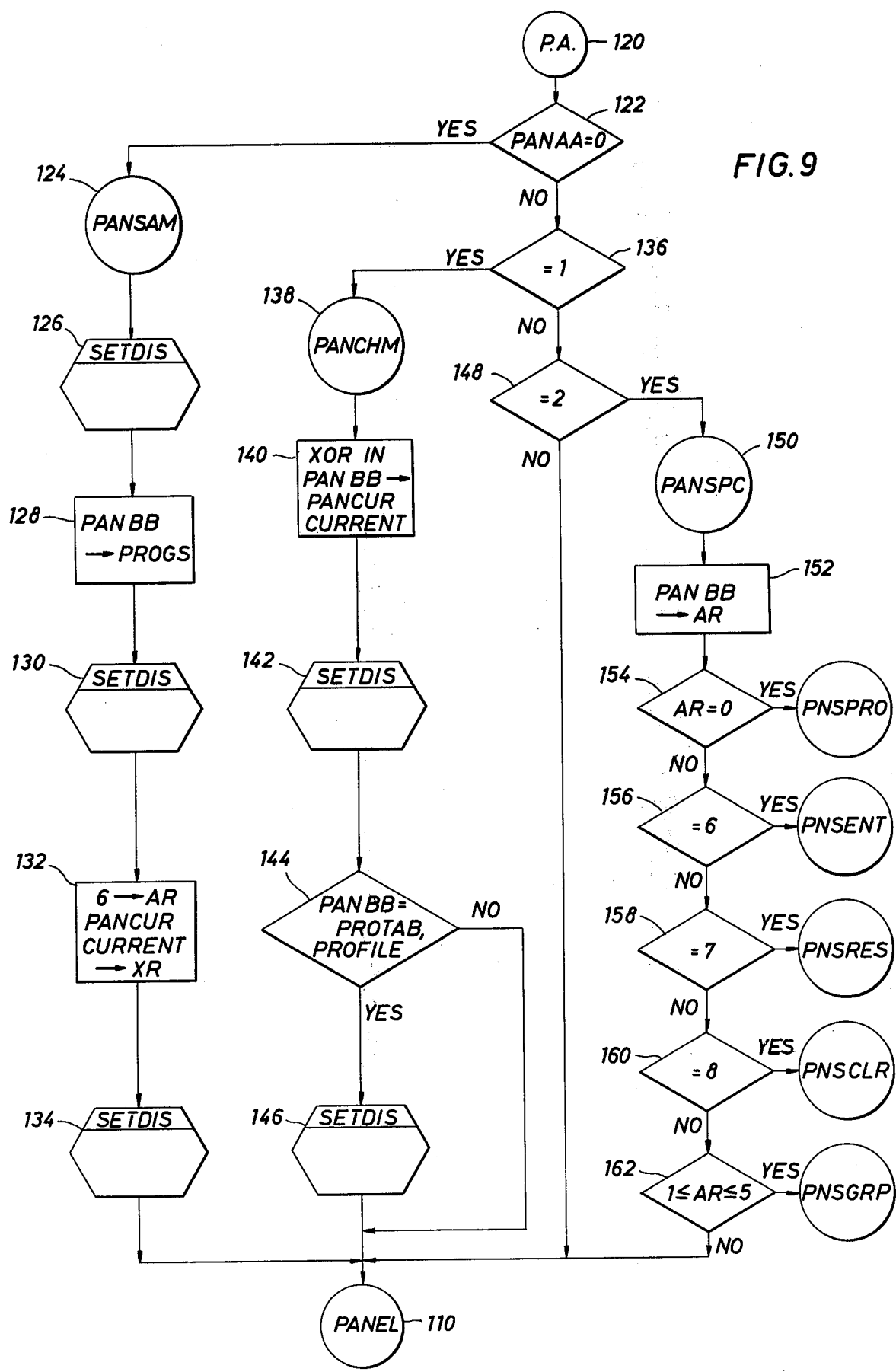

The PANKEY subroutine illustrated in FIG. 8 as block 116 proceeds at block 118 with the loading of the contents of the PANBYT register into an A register of the computer 80. The two most significant digits of the eight bit content of the PANBYT register are loaded into locations referred to as PAN AA and the six least significant digits are loaded to locations referred to as PAN BB. These digits have significance as described with respect to the description of the loading of the ROM 74 with respect to FIG. 5 above. At the completion of block 118, the program proceeds to program branch PA at block 120. The routine following the program branch PA, again denoted 120, is illustrated in FIG. 9. The value of PAN AA is examined. As described above, PAN AA can have a binary value of 00 indicative of a sample position number, 01 indicative of an individual test selection, or 10 indicative of depression of a button 51 in the function selector group 23 (FIG. 1). At decision block 122, the value of PAN AA is examined. If it is equal to 0, block 124, PANSAM, follows leading to block 126 at which the SETDIS subroutine is operated to turn off the lamps driven by the lamp driver 87 in response to the value in the PROGS register of the computer 80 as decoded by the decoder 85 (FIG. 5). The value PAN BB is loaded into the PROGS register at block 128 and, at back 130, through the SETDIS subroutine the value in the PROGS register is again coupled to the decoder 85. The value 6 is loaded into the A register to indicate a status for a following SETDIS subroutine, and the value in PANCUR current is loaded into the X register, at block 132. FIG. 12 illustrates the contents of the PANCUR register, sample position numbers are illustrated in a column. Adjacent rows are illustrated as having X's therein to illustrate that tests have been selected, one test corresponds to each column in which an X may be placed. PANCUR-current refers to the locations corresponding to the current enabled position. At block 134, SETDIS is again called for illuminating the proper lights at the control station 10. After block 134, a return is made to the panel subroutine 110 (FIG. 8).

If at block 122 it is determined that PANN AA is not equal to 0, PAN AA is next compared to 01. If PAN AA equals 01, at block 136, PANCHM subroutine 138 follows, and at block 140 an exclusive or, XOR, of the value of PAN BB with the contents of PANCUR-current is performed for loading into PANCUR-current. This provides the toggle function of selecting or deleting a test in response to alternate actuations of a switch 52. Block 142 following is the SETDIS subroutine. At block 144, a determination is made as to whether selection of individual tests has resulted in effectively selecting a panel or profile. The value of PAN BB is individually compared to a value which would indicate a profile and to each of values in locations of a PROTAB register further described below which define panels. If equality to a value indicative of a profile or panel is found at block 146, SETDIS is again run to illuminate the indicators 56-16 to 56-22 lights corresponding to a profile or panel for which on equality is found, and a return is made to panel routine 110. If not, panel routine 110 is directly returned to.

If at block 136 the comparison indicates that PAN AA is not equal to 01 then block 148 is proceeded to. If the value of PAN AA is binary 01 or decimal 2, PANSPC subroutine 150 follows and the value of PAN BB is delivered to the A register at block 152. Blocks 154 through 162 follow. The decimal equivalent of the value of PAN BB is respectively compared at each of these blocks to 0, 6, 7, 8, or 1 through 5. If an equality is found at any one of these comparisons, the program branches to a subroutine identified and further discussed with respect to FIG. 10. If there is no equality, there is an error. This may indicate the request for service was actually a noise spike. A return to panel routine 110 occurs to await an operator selection. At block 148 if PAN AA was equal neither 00, 01 or 02 then an error has occured, and a return to the panel routine 110 is indicated.

Figure 10:
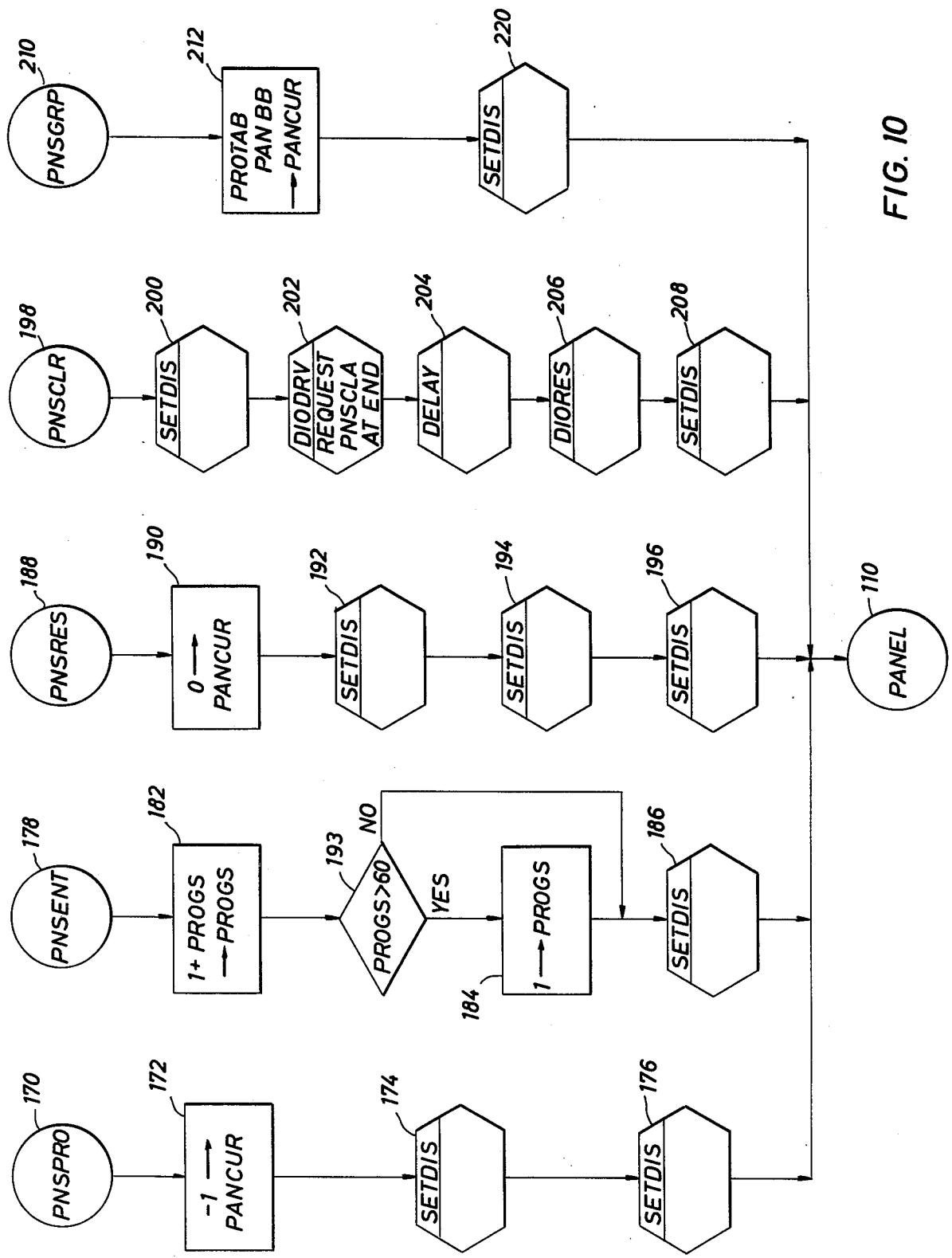

FIG. 10 illustrates the subroutines which can be branched to depending on the result of the comparison following block 152 in FIG. 9. All these subroutines conclude in a return to panel subroutine 110 (FIG. 7). It should be remembered that the PANSPC routine 150 can only be reached if PAN AA equals 10, in other words, if a button 51 has been depressed in the function selector group 23 (FIG. 3). If the value of PAN BB is 0, then PNSPRO routine 170 is called to command execution of a profile. At block 172 a value of minus 1 is loaded into PANCUR-current row to indicate selection of all tests (which would be illustrated by an X in each column of the row PANCUR-current in FIG. 12). At block 174 the SETDIS subroutine reads register values set to illuminate chemistry lamps 56-1 through 56-16 for selected chemistries. After this is done at block 176, the SETDIS subroutine operates to illuminate group and profile lamps 56 in the function selector means 23. Return to the panel routine 110 follows. If at block 156, the decimal equivalent of the value PAN BB was six, as described above, this indicates that a next position from the currently enabled position is to be enabled. PNSENT routine 178 follows. At block 180, the value in the PROGS register indicative of current position in incremented by one. In the present embodiment there are sixty positions. Provision is made for the possibility of a "carry" at block 182 at which the incremented value in the PROGS register is compared to sixty at block 183. If it is greater than sixty, then the next position is not position 61, since there is none, but position 1.

Therefore, at block 184, one is loaded into the PROGS register to indicate that the next channel is one. Block 186 follows at which the SETDIS subroutine is called. If the value in the PROGS register is not greater than sixty, then block 186 is proceeded to directly to from block 182 to run the SETDIS subroutine and the return to panel subroutine 110 then occurs.

If at block 158 in FIG. 9, the value of PAN BB has a decimal equivalent of seven, a reset is indicated and subroutine PNSRES is branched to at block 188. At block 190, the value 0 is loaded into PANCUR for the current row as indicated by the value in the PROGS register to indicate that no tests are commanded for the currently enabled channel. At block 192, SETDIS is run to clear the chemistry lamps 56-1 through 56-16. At block 194 SETDIS is again run to clear the group lamps 56-17 through 56-21, and at block 196, SETDIS is again run to clear the profile lamp 56-22, after which a return to the panel 110 occurs.

If at block 160, the decimal equivalent of the value of PAN BB is eight, then a master clear has been commanded to clear all tests commanded for all positions. The PNSCLR subroutine 198 is branched to. The program is arranged so that a master clear is not immediately executed. In this manner, accidental clearing of all test instructions for commanded tests is prevented. At block 200, SETDIS is run to blink the lamp 56-25 to acknowledge that the button 51-25 has been depressed. At block 202, a one byte input is provided in a DIODV subroutine to request the PNSCLA routine (FIG. 4) at "END", i.e., at block 114 of the panel subroutine 110 (FIG. 7). At block 204 a delay is initiated, and at block 206, if the button 51-25 has not been depressed again within the delay period, at block 206 the acknowledgment input is cancelled. At block 208, the SETDIS subroutine is run to stop the lamp 56-25 from blinking and a return to the panel subroutine 110 is made.

If at block 162, the value of PAN BB is from 1 to 5, PNSGRP subroutine 210 is branched to since this value is indicative of commanding of a panel, which is a group of tests. At block 214 as seen in FIG. 13, there is a word PROTAB which is accessed from the PROTAB register by the value of PAN BB. The contents of PROTAB are functionally illustrated in FIG. 13. The number indicates the value of PAN BB, and X's indicate that each value of PAN BB corresponds to different tests. Each accessed word is indicative of the particular tests in the particular panel. The accessed word is loaded into PANCUR current to select the tests within the panel. At block 220 SETDIS is operated to turn on the panel or test group lamp 56 corresponding to the panel button 51 which was depressed. Subroutine 110 is returned to.

The set display or SETDIS subroutine which is called as indicated above at various program positions is indicated as subroutine 230 in FIG. 11. At block 232, the current values in the A register and X register are saved at another location. At block 233, the contents of an event register in the computer 80 are loaded into the A register. Means in the computer 80 provide a value to the event register indicative of the type of data which initiated the request for service at the status circuit 79 (FIG. 5). A set of values is preselected for provision to the event register for supply to the A register in correspondence with the mode of updating in the SETDIS subroutine. In the present embodiment, the event register is loaded with the value of 3 when an update of the displays 24 and 25 (FIG. 1) is called for, and a positive sign not equal to three is provided to signal extinguishing of selected lamps 36, 37 or 50. A negative value is provided to indicate illumination of the selected lamps 36, 37 or 56. At block 234, the decimal equivalent of the value in the A register is compared to the value 3. If it is equal, then a command for updating the numbers displayed in the displays 24 and 25 (FIG. 1) is indicated and operation proceeds to block 236 at which the locations in the Word register corresponding to elements of the displays 24 and 25 are cleared and updated digits are supplied thereto. If the A register is not equal to three, operation proceeds to block 238 at which the information bit represent a display update put into a corresponding position in a mask having the same format as the data in the Word register and loaded into a SETMSK register. As described above, the Word register contents consists of eleven words, each sixteen bits long. Each bit is uniquely associated with one of the lamps 36, 37 or 56 or to each element of each digit of the digital displays 24 and 25. At block 240, it is determined if the A register is less than 0. If so, then display elements are to be extinguished. The contents of the SETMSK register are complemented and are reloaded therein. The contents, WORD and SETMSK are ANDed and loaded into the Word register. If the value of the A register is not less than 0, then the contents WORD value ORed with the contents SETMSK loaded into the Word register to provide an output for driving the displays. After blocks 242, 244 or 236, the I/O routine, DIODRV is called at block 246 to result in transferring the values from the computer 80 to the decoder circuit 85. Consequently, all lamps are properly operated to be illuminated in accordance with the most recent data update. At block 247, the values saved at block 232 are restored to the A and X registers. At block 248 a return to the routine is indicated from the branch made to the SETDIS routine.

FIG. 14 is illustrative of a master clear routine PNSCLA 250. This routine is requested in response to depression of a master clear button 51-25 (FIG. 1) as indicated at block 160 of FIG. 9 and block 198 of FIG. 10. As described with respect to FIG. 10, a master clear button is pushed once and acknowledged to set the lamp there behind blinking. However, a master clear will not be performed unless the master clear button is pushed again within a prescribed time. At block 252 it is determined if the master clear button 51-26 (FIG. 1) was again depressed within a prescribed time. If not, the program returns to panel subroutine 110. If it has been depressed, operation proceeds to block 254 which is a delay subroutine. The time out sequence is halted and at block 256, one is loaded into the PROGS register to indicate that position 1 will next be enabled and 0 is entered into PANCUR for all positions. In this manner all tests are cleared. At block 258, SETDIS routine is called. Since all tests have been cleared, all lamps will be extinguished. At block 260, SETDIS is again run to respond to the value 1 now in the PROGS register to illuminate the lamp 36-1. At block 262, SETDIS is again run to clear the group and profile lamps 56. Panel routine 110 is then returned to.

What is thus provided is a unique system in which complete selectivity is provided for in selection of tests which may be performed by an automatic chemical testing apparatus with efficient utilization of hardware. Further, operator utilization is facilitated due to the operation of indicator means which may be easily read by an operator to indicate fully the status of all test commands. The foregoing specification will enable those skilled in the art to make many modifications in the specific embodiments shown while providing for test command and indication means which are constructed in accordance with the present invention.

What is claimed is new and desired to be secured by Letters Patent of the United States is:

1. In an automatic chemical testing apparatus for performing tests on each of a plurality of liquid samples, each sample having an ordinal position, including means for performing tests on selected aliquots of a liquid sample, and a reaction container for holding each aliquot, test selection means for selecting a test or tests to be performed on each sample, instruction means for producing instructions in response to actuation of said test selection means, instruction storage means coupled to said instruction means, control means coupled to said instruction storage means, reagent injecting means coupled for control by said control means for initiating tests in selected reaction containers in response to stored instructions and readout means coupled to said control means for analyzing reacted contents of the selected reaction containers, the improvement wherein said test selection means comprises: a first group of position selector means, each position selector means being associated with one sample position, and further comprising first and second indicator means associated with each position selector means, a second group of selector means, each selector means being associated with one or a group of said different chemical tests, said instruction means being coupled between said first and second groups of selector means and said instruction storage means such that actuation of one of said position selector means in said first group enables programming of tests to be performed on the sample position to which said selector means corresponds such that a current enabled position is provided and wherein operation of selector means in said second group produces a signal for storage in correspondence to said enabled position, sensor means in said control means responsive to all of said selector means for producing an output signal for operating said first indicator means associated with one said first selector means in response to actuation of said one selector means and for deenergizing the said first indicator means when a different position selector means is actuated and for producing a signal for energizing said second indicator means in response to programming of a test or tests for said one position.

2. The improvement according to claim 1 further comprising further indicator means associated with each of said second selector means and means in said sensor means responsive to test selection for operating said further indicating means to indicate the condition of the associated test having been selected for the current enabled position.

3. The improvement according to claim 2 wherein said second selector means comprises a first plurality of selector means, each associated with one test and a second plurality of selector means, each associated with a preselected group of tests.

4. The improvement according to claim 3 wherein each of said selector means comprises a switch and each of said indicator means comprises a lamp.

5. The improvement according to claim 4 further comprising counting means for registering the sample position of the sample currently at said fluid transfer means and the position of said sample currently at said readout means, and further comprising display means for displaying said numbers.

6. The improvement according to claim 5 wherein said control means further comprises a test selection switching means and means for enabling a next position selected with respect to a current enabled position in said first group of selector means in response to actuation of said test selection switching means.

7. The improvement according to claim 6 further comprising data entry means coupled to said instruction means for selecting the tests associated with each of said second plurality of selector means within said second group of selector means.

8. The improvement according to claim 7 further comprising reset means coupled to said control means for providing a signal upon actuation to clear currently programmed instructions for a currently enabled channel.

9. The improvement according to claim 8 further comprising master reset means coupled to said control means for producing a signal for clearing all program signals and deenergizing all indicator means and for subsequently enabling one preselected sample position.

* * * * *